(12) United States Patent
Chen et al.

(10) Patent No.: US 8,691,289 B2
(45) Date of Patent: Apr. 8, 2014

(54) METHODS OF TREATING OUTER EYE DISORDERS USING HIGH ORP ACID WATER AND COMPOSITIONS THEREOF

(75) Inventors: Yongge Chen, Guangzhou (CN); Roberto De Noni, Fregona (IT)

(73) Assignee: APR Nanotechnologies S.A., Balerna (CH)

( * ) Notice: Subject to any disclaimer, the term of this patent is extended or adjusted under 35 U.S.C. 154(b) by 636 days.

(21) Appl. No.: 12/816,731

(22) Filed: Jun. 16, 2010

(65) Prior Publication Data
US 2010/0330204 A1 Dec. 30, 2010

Related U.S. Application Data

(60) Provisional application No. 61/187,900, filed on Jun. 17, 2009, provisional application No. 61/239,912, filed on Sep. 4, 2009.

(51) Int. Cl.
*A61K 33/14* (2006.01)
*A61K 31/74* (2006.01)

(52) U.S. Cl.
USPC .................. 424/661; 424/78.04; 514/912

(58) Field of Classification Search
USPC ................. 424/78.04, 661; 514/912
See application file for complete search history.

(56) References Cited

U.S. PATENT DOCUMENTS

| | | | |
|---|---|---|---|
| 5,234,563 A | 8/1993 | Arai et al. | |
| 5,334,383 A | 8/1994 | Morrow | |
| 5,445,722 A | 8/1995 | Yamaguti et al. | |
| 5,474,662 A | 12/1995 | Miyamae | |
| 5,507,932 A | 4/1996 | Robinson | |
| 5,510,009 A | 4/1996 | Arai et al. | |
| 5,560,816 A | 10/1996 | Robinson | |
| 5,589,052 A | 12/1996 | Shimamune et al. | |
| 5,593,554 A | 1/1997 | Yamanaka et al. | |
| 5,616,221 A | 4/1997 | Aoki et al. | |
| 5,622,828 A | 4/1997 | Parma et al. | |
| 5,622,848 A | 4/1997 | Morrow | |
| 5,674,537 A | 10/1997 | Morrow | |
| 5,711,950 A | 1/1998 | Lorenzen | |
| 5,731,008 A | 3/1998 | Morrow | |
| 5,759,489 A | 6/1998 | Miura et al. | |
| 5,824,353 A | 10/1998 | Tsunoda et al. | |
| 5,900,127 A | 5/1999 | Iida et al. | |
| 5,965,009 A | 10/1999 | Shimamune et al. | |
| 5,980,703 A | 11/1999 | Yamada et al. | |
| 6,033,678 A | 3/2000 | Lorenzen | |
| 6,093,292 A | 7/2000 | Akiyama | |
| 6,126,796 A | 10/2000 | Shimamune et al. | |
| 6,126,810 A | 10/2000 | Fricker et al. | |
| 6,174,419 B1 | 1/2001 | Akiyama | |
| 6,186,148 B1* | 2/2001 | Okada ........................... 128/898 |
| 6,207,201 B1 | 3/2001 | Piacenza | |
| 6,235,186 B1 | 5/2001 | Tanaka et al. | |
| 6,258,222 B1 | 7/2001 | Nakamura et al. | |
| 6,296,744 B1 | 10/2001 | Djeiranishvili et al. | |
| 6,426,066 B1* | 7/2002 | Najafi et al. ................ 424/78.04 |
| 6,464,845 B2 | 10/2002 | Shirota et al. | |
| 6,527,940 B1 | 3/2003 | Shimamune et al. | |
| 6,632,347 B1 | 10/2003 | Buckley et al. | |
| 7,090,753 B2 | 8/2006 | Sumita | |
| 7,276,255 B2* | 10/2007 | Selkon ........................... 424/665 |
| 7,291,314 B2 | 11/2007 | Paskalov et al. | |
| 7,303,660 B2 | 12/2007 | Buckley et al. | |
| 7,323,118 B2 | 1/2008 | Calderon | |
| 7,393,522 B2 | 7/2008 | Najafi et al. | |
| 7,442,288 B2 | 10/2008 | Sumita | |
| 2002/0134691 A1 | 9/2002 | Satoh et al. | |
| 2003/0185704 A1 | 10/2003 | Bernard et al. | |
| 2004/0258836 A1 | 12/2004 | Besenhard | |
| 2005/0139808 A1 | 6/2005 | Alimi | |
| 2005/0142157 A1 | 6/2005 | Alimi | |
| 2005/0196462 A1 | 9/2005 | Alimi | |
| 2006/0235350 A1 | 10/2006 | Alimi et al. | |
| 2006/0241546 A1 | 10/2006 | Alimi | |
| 2006/0249375 A1 | 11/2006 | Aoun et al. | |
| 2006/0253060 A1 | 11/2006 | Alimi | |
| 2006/0275387 A1 | 12/2006 | Bagley | |
| 2007/0017820 A1 | 1/2007 | Anderson et al. | |
| 2007/0051640 A1 | 3/2007 | Bellamy | |

(Continued)

FOREIGN PATENT DOCUMENTS

EP 0933332 8/1999
EP 1036861 A1 9/2000

(Continued)

OTHER PUBLICATIONS

Anonymous, "Aquatech Amsterdam 2006 Press Information," [online] Aug. 28, 2006, URL:www.amsterdam.aquatechtrade.com/_upload/aquatech2006/docs/Noviteiten_supplement_ENG.doc.

Fenner, Dunja Corinne, "Antimicrobial activity of electrolyzed oxidizing water using standard in-vitro test procedures for the evaluation of chemical disinfectants", [online] Inaugural-Dissertation, Zurich Oct. 6, 2005, URL:http://www.water4u.net/file_download.php?filename=63ff8dbc4bb2121cc20add56549dcbe2.

Hayashi, Hidemitsu, "Benefits of Alkaline, Ionized Water" [online] Oct. 6, 2005, URL:http://www.ionizers.org/water.html.

Hayashi, Hideaki, et al., Artificial Organs, "Successful Treatment of Mediastinitis after Cardiovascular Surgery Using Electrolyzed Strong Acid Aqueous Solution," vol. 21, p. 39-42, 1997.

Hsu, Shun-Yao, et al., Journal of Food Engineering, "Effects of storage conditions on chemical and physical properties of electrolyzed oxidizing water," vol. 65, p. 465-471, 2004.

Kim, Yong Jeong, et al., "Suppression of cobalt dissolution from the $LiCoO_2$ cathodes with various metal-oxide coating", Database Compendex [online] Dec. 2003.

(Continued)

*Primary Examiner* — Zohreh Fay
(74) *Attorney, Agent, or Firm* — Clark G. Sullivan; Troutman Sanders LLP

(57) ABSTRACT

The present invention relates to a method of treating an outer eye disorder selected from a cataract, neovascularization, keratitis, epithelium deficiency, or chronic opacity, by administering to the eye a composition comprising acidic electrolytic water. The present invention also relates to a stable acidic electrolyzed oxidizing water characterized by low conductivity, the presence of dissolved chlorine gas ($Cl_2$), hypochlorous acid (HOCl) and chloride ions ($Cl^-$), and by the presence of negligible quantities of hypochlorite ion ($OCl^-$).

13 Claims, 5 Drawing Sheets

(56) References Cited

U.S. PATENT DOCUMENTS

| | | |
|---|---|---|
| 2007/0173755 A1 | 7/2007 | Alimi et al. |
| 2007/0196357 A1 | 8/2007 | Alimi et al. |
| 2007/0196434 A1 | 8/2007 | Alimi et al. |
| 2009/0181107 A1 | 7/2009 | Buckley et al. |
| 2009/0221989 A1 | 9/2009 | Najafi et al. |
| 2009/0258083 A1 | 10/2009 | Calderon |

FOREIGN PATENT DOCUMENTS

| | | |
|---|---|---|
| EP | 1007478 | 8/2003 |
| EP | 1036861 B1 | 10/2003 |
| EP | 1600426 | 11/2005 |
| EP | 1103264 | 5/2007 |
| EP | 1551770 | 3/2010 |
| JP | 04235904 | 8/1992 |
| JP | 06126287 | 5/1994 |
| JP | 11035472 | 2/1999 |
| JP | 2000229815 | 8/2000 |
| JP | 2001096272 | 4/2001 |
| WO | WO97/19707 | 6/1997 |
| WO | WO2004/078654 | 9/2004 |
| WO | WO2005/065383 | 7/2005 |
| WO | WO2007/048772 | 5/2007 |
| WO | WO2008/091032 | 7/2008 |
| WO | WO2008/131936 | 11/2008 |

OTHER PUBLICATIONS

Kim, Tae-Joon, et al., Electrochimica Acta, "Enhanced electrochemical properties of $SnO_2$ anode by $AlPO_4$ coating", vol. 49, No. 25, p. 4405-4410, 2004.

Len, Soo-Voon, et al., J. of Agric. Food Chem., "Effects of Storage Conditions and pH on Chlorine Loss in Electrolyzed Oxidizing (EO) Water," vol. 50, p. 209-212, 2002.

Nakagawara, Shunji, et al., Analytical Sciences, "Spectroscopic Characterization and the pH Dependence of Bactericidal Activity of the Aqueous Chlorine Solution," vol. 14, p. 691-698, 1998.

Venkitanarayana, Kumar S., et al., "Efficacy of Electrolyzed Oxidizing Water for Inactivating *Escherichia coli* O157:H7, *Salmonella enteritidis*, and *Listeria monocytogens*," Applied Enviro. Microbiology, vol. 65, No. 9, p. 4276-4279, 1999.

Yang, Gordon C.C., et al., J. of Membrane Science, "Reclamation of high quality water from treating CMP wastewater by a novel crossflow electrofiltration/electrodialysis process," vol. 233, p. 151-159, 2004.

International Search Report PCT/EP2008/003383 dated Jun. 9, 2009.

International Preliminary Report on Patentability and Written Opinion for PCT/EP2008/003383 dated Oct. 27, 2009.

International Search Report for PCT/EP2006/067676 dated Jan. 11, 2007.

International Preliminary Report on Patentability and Written Opinion for PCT/EP2006/067676 dated Apr. 29, 2008.

\* cited by examiner

METHODS OF TREATING OUTER EYE DISORDERS USING HIGH ORP ACID WATER AND COMPOSITIONS THEREOF

This application claims priority to U.S. Provisional App. Nos. 61/187,900 filed Jun. 17, 2009, and 61/239,912, filed Sep. 4, 2009. The content of these earlier applications is incorporated herein by reference.

FIELD OF THE INVENTION

The present invention relates to pharmacological methods of treating outer eye disorders using acid water having a high oxidation reduction potential (ORP) and compositions thereof.

BACKGROUND OF THE INVENTION

Outer Eye Disorders

The outer eye includes several organs, including the cornea, the iris and the lens. The iris is a membrane in the eye, responsible for controlling the amount of light reaching the retina. The cornea and lens refract light onto the retina. Healthy eyes produce clear vision as the result of the transparency of the cornea and lens. Cataract, a clouding of the lens of the eye, can obstruct the passage of light and result in a gradual loss of vision. Unfortunately, very few treatments exist for cataract, other than to replace the cataractous lens with an artificial lens through a complicated surgical procedure.

Disorders such as keratitis, neovascularization, and epithelium deficiency can also reduce vision by interfering with the transparency of the cornea. These disorders can result from numerous causes, including viral and bacterial infections, trauma and surgery. Antibiotics and anti-viral agents are often used to treat infectious causes, but in many instances the patient has no choice but to undergo a complicated surgical procedure to remove damaged tissue before it can scar and reduce eyesight.

PCT Publications WO 2004/012748 and WO 2001/054704 teach an isotonic ionized acidic solution for wound care, and tout the water based upon its antioxidant characteristics and antimicrobial properties. The publications state that the solution may be used in the place of saline in ophthalmic applications such as contact lens cleaning solutions or for irrigation of the eye during ophthalmic surgery, and that the properties of the solution depend on the particular concentration ranges of a mixture of salts.

There remains a need for pharmacological methods of treating outer eye disorders, especially those that affect the cornea and lens. There is particularly a need to methods that prevent further deterioration of vision in the eye, and that potentially improve the vision of the patient whose vision has worsened.

High ORP Acid Water

It is known that aqueous solutions of salts, particularly sodium chloride, as a consequence of an electrolytic treatment, are split into two liquid products, one having basic and reducing characteristics (generally known as cathode water or alkaline water) and another (generally known as anode water or acid water) having acid and oxidizing characteristics.

Conventional electrolytic waters suffer the acknowledged drawback of having very limited preservation. A few days after preparation, the product in fact generally tends to degrade and lose its properties. Known electrolytic waters, therefore, must be prepared and used substantially on the spot. Accordingly, the commercial utilization of the product in itself is extremely disadvantageous, since the shelf life of any ready-made packages is dramatically limited.

The stability of an electrolyzed oxidizing water is reported in the article "*Effects of Storage Conditions and pH on Chlorine Loss in Electrolyzed Oxidizing (EO) Water*"—Journal of Agricultural and Food Chemistry—2002, 50, 209-212 by Soo-Voon Len, et al. In Soo-Voo Len, electrolyzed water with an acidic pH (2.5-2.6), high OPR (1020-1120 mV), and a free chlorine content of ~50 ppm (53-56 ppm) was generated using a current intensity of 14 Ampere and 7.4 Volt. Unfortunately, in an open condition at 25° C., the chlorine in the electrolyzed water was completely lost after 30 hours when agitated, and after 100 hours when not agitated. Furthermore, in a closed dark condition at 25° C., the free chlorine in the electrolyzed water decreased by approximately 40% after 1400 hours (about 2 months).

The stability of electrolyzed oxidizing water also is reported in the article "*Effects of storage conditions on chemical and physical properties of electrolyzed oxidizing water*"—Journal of Food Engineering 65 (2004) 465-471 by Shun-Yao Hsu, et al. In Shun-Yao Hsu, the electrolyzed water of "formulation J" had an acidic pH (2.61), high OPR (1147 mV), and a free chlorine content of 56 ppm. The article reports that in a closed condition at 25-30° C., the free chlorine in the electrolyzed water was 43 ppm after 21 days, a 23% loss.

Thus, there remains a need for acidic electrolytic water with a greater chemical stability than traditional waters. There is a particular need for water with a greater stability during long term storage, so as to allow for the commercial utilization of acidic electrolytic water products.

SUMMARY OF THE INVENTION

It has unexpectedly been discovered that acidic water, having a high oxidation reduction potential, promotes and facilitates an ordered regeneration of the eye when impacted by negative environmental stimuli such as infections and trauma, or metabolic processes such as aging and diabetes. In particular, it has been discovered that the water fosters a healthy epithelium on the cornea, reduces uncontrolled corneal neovascularization, and encourages ordered protein synthesis in the lens. The water can thus be used to treat various outer eye disorders that affect the cornea, lens or iris, including cataract, keratitis, neovascularization and epithelium deficiency.

Therefore, in one embodiment, the invention provides a method of treating an outer eye disorder selected from cataract, keratitis, corneal neovascularization and epithelium deficiency in an animal patient in need thereof, comprising topically administering to an eye of said patient a composition comprising a therapeutically effective amount of a high ORP acidic water. The composition is preferably in the form of an eye drop. In another embodiment, the invention provides a method for improving opacity in a lens of an animal patient in need thereof, comprising administering to an eye of said patient a composition comprising a therapeutically effective amount of a high ORP acidic water.

The methods can be performed ad libitum in response to observable irritation. An effective treatment for these disorders typically requires a plurality of administrations, extending days, months or even years of the patient's life. The water can be defined by several characteristics, including pH and ORP, in addition to other characteristics including cluster size (as measured by NMR half line width), and the content of various chlorine/chloride species.

It also has unexpectedly been discovered that acidic nanoclustered water having a particular composition of chlorine species has a greater chemical stability than traditional waters. The unique composition can result from particular membrane and electrodes used in the electrolyzing equipment, which can produce a high current intensity without causing the electrodes to break up on their surface and release heavy metals that may adversely affect stability.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
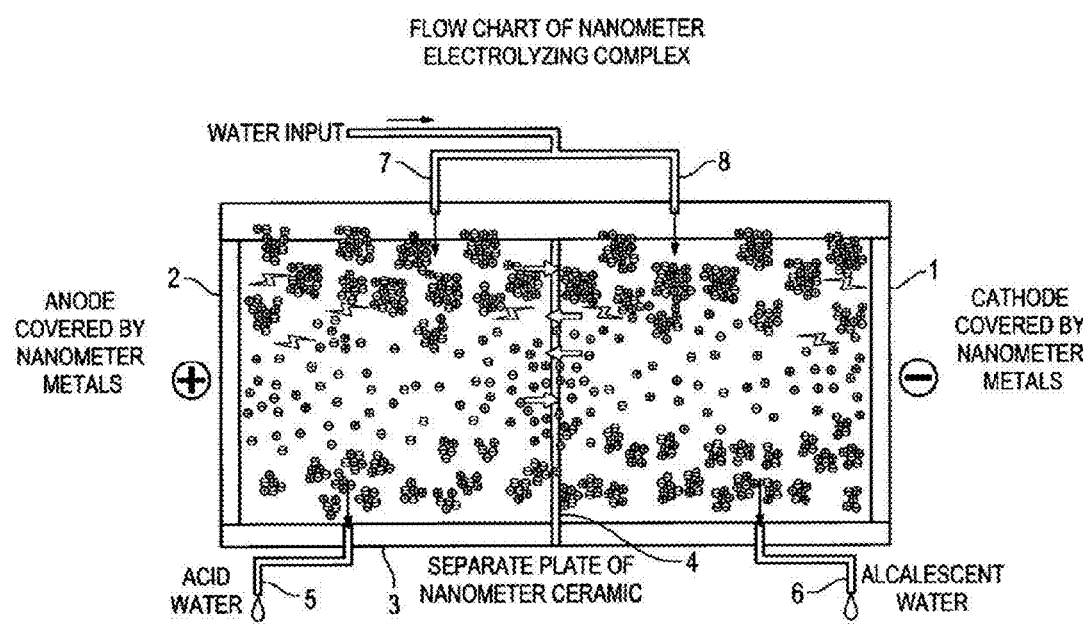
FIG. 1 is a schematic view of an electrolytic device comprising an electrolysis chamber and two electrodes.
Figure 2:
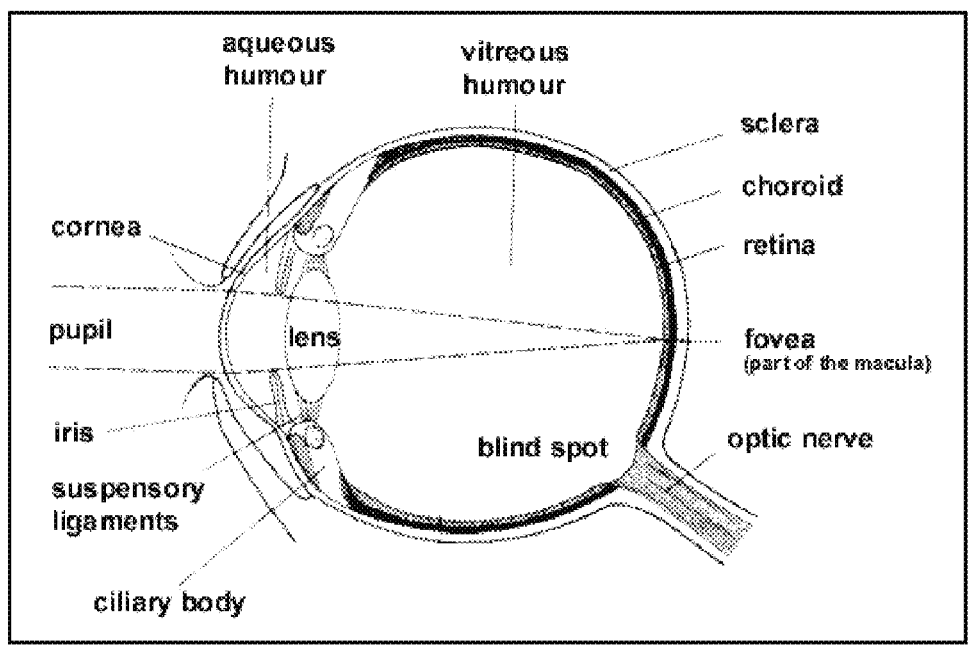
FIG. 2 is side cross-view of a human eye, depicting the various components of the eye.

The present invention may be understood more readily by reference to the following definitions and detailed description of preferred embodiments of the invention and the non-limiting Examples included therein.

Definitions and Use of Terms

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "fluid" is used to reference any pure fluid, solution or suspension which is capable of producing a non-spontaneous chemical reaction if subjected to electrolysis. One highly preferred fluid is water. The term "water" is used to reference any type of water, such as tap water, filtered water, deionized water, and distilled water. Once subjected to electrolysis, the water separates into two liquid fractions, which for the sake of simplicity are referenced here as acid water or anode water and as cathode water or alkaline water.

The term "high ORP water" refers to water having an oxidation reduction potential greater that +600. The ORP preferably ranges from +600 to +1350 mV, more preferably from +800, +900, or +1000 mV to +1300 mV, most preferably from +1100 to +1250 mV.

The term "acid water" or "acidic water" refers to water having a pH less than 7.0. The pH of the acid water preferably ranges from 0.5, 1.0 or 2.0 to 6.5, 6.0, 5.0, 4.0, or 3.0, and most preferably ranges from 1.0 to 4.0.

The term "electrolytic water," when used herein, means water produced by the process of electrolysis, and is preferably characterized by an oxide reduction potential (ORP) and/or pH that reflects its acid or alkaline nature.

The term "nanoclustered water," when used herein, refers to water having a reduced cluster size, typically induced by electrolysis. The size of the cluster can be measured by its NMR half line width, and in preferred embodiments the water has a NMR half line width using $^{17}O$ of less than about 60, 56, or 52 Hz, preferably greater than about 42 or 45 Hz.

As used herein, "therapeutically effective amount" refers to an amount sufficient to elicit the desired biological response. The therapeutically effective amount or dose can depend on the age, sex and weight of the patient, and the current medical condition of the patient. The skilled artisan will be able to determine appropriate dosages depending on these and other factors in addition to the present disclosure.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

When the context allows, the term "significantly" can be interpreted to mean a level of statistical significance, in addition to "substantially." The level of statistical significance can be, for example, of at least $p<0.05$, of at least $p<0.01$, of at least $p<0.005$, or of at least $p<0.001$. When a measurable result or effect is expressed or identified herein, it will be understood that the result or effect can be evaluated based upon its statistical significance relative to a baseline.

The term "outer eye disorder," as used herein, refers to any disorder of the cornea, iris or lens, that is associated with irregular growth or structuring of protein or cellular components. Examples of outer eye disorders include keratitis, neovascularization, epithelium deficiency and cataracts. The keratitis can be superficial, ulcerative (i.e. corneal ulcer), hypopyon (i.e. hypopyon ulcer), mycotic (caused by fungus), or deep (perforating through all layers of cornea). Furthermore, the keratitis may result from bacteria, vitamin A deficiencies, viruses, trauma (usually following insertion of an object into the eye), abrasion, surgery, fungi, or parasites. The neovascularization can be localized, deep, or resulting in buildup of tissue (pannus). Furthermore, the neovascularization can result from, or be associated with a lack of oxygen to the eye, trauma, abrasion, surgery, age related macular degeneration, inflammation and myopia.

The term "cataract," as used herein, refers to a variety of conditions that create a cloudy or calcified lens that obstructs vision. The cataract can be an infantile, juvenile, or presenile cataract. Alternatively, the cataract can be an age-related or senile cataract. Furthermore, the cataract can be either a traumatic cataract or a congenital cataract. The cataract can be located in a variety of regions within the lens. For example, the cataract can be an anterior subcapsular polar cataract (within the front, center lens surface), a posterior subcapsular polar cataract (within the rear, center lens surface), a cortical cataract (radiating from the center to the edge of the lens), a nuclear cataract (in the center of the lens), or combinations thereof. The cataract can also be associated with other disorders, such as diabetic cataract and toxic cataract. Furthermore, the cataract can be at a variety of stages such as immature cataract (partially opaque lens), mature cataract (completely opaque lens), or hypermature cataract (liquefied cortical matter, also known as a Morgagnian cataract).

Throughout the description and claims of this specification, the word "comprise" and variations of the word, such as "comprising" and "comprises," means "including but not limited to," and is not intended to exclude, for example, other additives, components, integers or steps.

As used in the specification and the appended claims, the singular forms "a," "an" and "the" or like terms include plural referents unless the context clearly dictates otherwise. Thus, for example, reference to "an ingredient" includes mixtures of two or more ingredients, and the like. The word "or" or like terms as used herein means any one member of a particular list and also includes any combination of members of that list.

Discussion

As discussed above, it has now been discovered that acidic electrolyzed water can be used to effectively treat patients suffering from outer eye disorders. This discovery is based on the results of experimentation described in the "Examples" below, which revealed that a composition of acidic nanoclustered water, unlike saline, affects the healing of the eye in a way that can be very useful in fostering correct protein and cellular structure and organization, and reducing opacity in the cornea and lens. It also has been discovered that acidic electrolyzed water of a particular chemical composition can remain stable for significantly longer period of time than previous electrolyzed oxidizing waters.

Therefore, in one embodiment, the invention provides a method of treating an outer eye disorder selected from cataract, keratitis, corneal neovascularization and epithelium deficiency in an animal patient in need thereof, comprising topically administering to an eye of said patient a composition comprising a therapeutically effective amount of a high ORP acidic water. The composition is preferably in the form of an eye drop.

Importantly, the method can decrease opacity of the lens, reduce loss of vision, increase visual acuity, increase contrast sensitivity, and reduce halos. Therefore, in another embodiment, the invention provides a method for improving opacity, reducing loss of vision, increasing visual acuity, increasing contrast sensitivity, or reducing halos in a lens of an animal patient in need thereof, comprising administering to an eye of said patient a composition comprising a therapeutically effective amount of a high ORP acidic water.

The step of administering the composition can be performed between 1 and 20 times per day using any method known in the art, but is preferably undertaken more than once during a 24 hour period. The administration can be carried out for a period of time including one week, 10 days, two weeks, three weeks, one month, or continually as a maintenance therapy. In a particular embodiment, the administration step comprises dropping the composition directly into the eye. In another embodiment, the administration step comprises applying the composition to the eye with gauze. In yet another embodiment, the administering step comprises applying the composition to the eye with an eye washer.

The method can further comprise, before the administering step, diagnosing said eye as having a cataract or other outer eye disorder.

The step of administering the composition can be performed between 1 and 4 times per day using any method known in the art. The administration can be carried out for a period of time including one week, 10 days, two weeks, three weeks, one month, or continually as a maintenance therapy. In a particular embodiment, the administration step comprises dropping the composition directly into the eye. In another embodiment, the administration step comprises applying the composition to the eye with gauze. In yet another embodiment, the administering step comprises applying the composition to the eye with an eye washer.

The method can further comprise, before the administering step, performing surgery on said eye.

The Acid Waters

Acid water can be obtained with a water electrolysis method as described below. The electrolytic acid waters can differ from similar products substantially in their stability, which is at least partly due to the higher performance of the nano-coated electrodes and the electrolysis process. In conventional processes, even when the water is subjected to a filtration step before electrolysis, the electrodes tend to break up on their surface during the process, releasing large amounts of heavy metals (particularly of the metal or metals of which the cathode and anode are made). However, these acid waters can be free from heavy metals because said metals, if present, are present in a quantity which is below the limits that can be detected with ordinary analytical methods. For example, the water according to the invention can have a cadmium concentration of less than 5 µg/l, less than 10 µg/l of chromium, less than 5 µg/l of lead, and less than 20 µg/l of nickel. Suitable test methods for these heavy metals are described in Table 1 below:

TABLE 1

Heavy Metal Testing Methods

| TEST | TESTING METHOD |
|---|---|
| Cadmium | APAT CNR IRSA 3120/2003 |
| Total Chromium | APAT CNR IRSA 3150/2003 |
| Lead | APAT CNR IRSA 3230/2003 |
| Nickel | APAT CNR IRSA 3220/2003 |
| Fixed Residue at 180° C. | APAT CNR IRSA 2090A/2003 |

Although one does not intend to be bound to any particular theory, it is believed that the absence of heavy metals is one of the main reasons for the unusual and advantageous stability over time of the electrolytic acid water. The expression "stability over time" is used to mean that the acid water, if kept sheltered from the light, air and heat, keeps its chemical and physical properties, particularly its pH, ORP and/or NMR half line width, substantially unchanged for greater than 60 or 90 days, preferably greater than 180 days, even more preferably greater than 365 days, up to two, three or even five years. By substantially unchanged, it is meant that the property under evaluation does not vary by more than 50, 30, 15, 10, 5, or even 3% during the applicable time frame.

Although the stability time depends on the steps taken to preserve the solution, it must be noted that for equal storage conditions, an acidic water obtained by using an electrolytic device as defined above has shown a distinctly higher stability than known similar products, which in the best cases have shown a shelf life of only 60-90 days. Therefore, these products must be obtained and used over a short period or even simultaneously with their production. Therefore, the electrolytic acidic water according to the invention can be useful also for applications in locations (Third World countries) and situations (scarcity of water to provide electrolysis) in which favorable conditions for its production are not available.

The ORP of the electrolytic acid water preferably ranges from +600 to +1350 mV, more preferably from +800, +900, 1000 or +1100 mV to +1300, 1250 or +1200 mV, most preferably from +1100 to +1250 mV. The pH of the acid water preferably ranges from 0.5 or 1.0 to 6.5, 6.0, 5.0, 4.0, or 3.0, and most preferably ranges from 1.0 to 4.0.

Nuclear magnetic resonance $^{17}O$ NMR measures, particularly when evaluated at the half way point of the water peak, are useful to measure the quality of acid waters of the current invention, because they reflect intrinsic properties of the water structure such as the median molecular cluster size of $H_2O$ molecules, and the distribution of molecular cluster sizes, in addition to contaminants such as ionic species within the water. The expression "molecular cluster" designates the number of molecules of water which are coordinated in an ordered structure In most preferred embodiments, the $^{17}O$ NMR half line width for the acid water is equal to or greater than 42, 45, 46, or 47, and less than 100, 75, 60, 56, 53, 51, 50 or 49 Hz, wherein the range can be selected from any of the foregoing endpoints. Thus, for example, in preferred embodiments, the acid water of the present invention has an NMR half line width ranging from 45 to less than 51 Hz, or 45 to less than 50 Hz, or 46 to less than 50 Hz.

The acid water may also be characterized by the presence and quantity of chlorine species in the water. One of the following assays or any combination of the following assays may be used to characterize the water. According to the free chlorine assay (spectrophotometric method), or the total chlorine assay (spectrophotometric method), the water may be defined as containing less than 85, 70, 60, 55, 52 or even 50 mg/l of chlorine species, optionally limited by a lower bound of 20, 30 or 40 mg/l. According to the total chlorine assay (iodometric method), the water may be defined as containing less than 80, 70, 65, or even 62 mg/l of chlorine species, optionally limited by a lower bound of 20, 30 or 40 mg/l. According to the UNI 24012 (Mercurimetric method) chloride assay, the water may contain greater than 50, 100, 130, 150 or even 170 mg/l of chloride, and/or less than 250 or 200 mg/l. Chlorites (as $ClO_{2-}$), when measured by EPA 300.1 (1997) (detection limit 100 ug/l), are preferably non-detectable. Chlorates ($ClO_{3-}$), when measured by EPA 300.1 (1997) (detection limit 0.1 mg/l), are preferably present in an amount less than 10, 5, 2, or even 1 mg/l.

Although in certain embodiments the acid water may contain oxidizing chlorine species in amounts of up to 60 or even 100 mg/l, in a preferred embodiment the acid water according to the invention is essentially free of oxidizing chlorine species, or other anionic residues of salts that are generated during the electrolytic process, i.e. less than 10 or even 5 mg/l, and preferably undetectable.

In a particularly desirable embodiment, the water can be characterized by conductivity, the presence of dissolved chlorine gas ($Cl_2$), hypochlorous acid (HOCl) and chloride ions ($Cl^-$), and by the presence of negligible quantities of hypochlorite ion ($OCl^-$). In water, the relative amount of chlorine and hypochlorous acid is strongly affected by the amount of chlorides. Specifically, an increase in chlorides results in an increase in the amount of chlorine gas with respect to hypochlorous acid as according to the following equilibrium:

Because of the relationship between the amount of chlorides and the amounts of chlorine gas and hypochlorous acid, the amount of chloride in the water is preferably very low (less than 200 ppm) to ensure that the free chlorine in the water is almost exclusively in the form of hypochlorous acid.

The relationship between the four species $Cl_2$, HOCl, $Cl^-$, and $OCl^-$ can be understood using the disassociation equilibria of gaseous chlorine in water as described below, in which $Cl_2$, HOCl, and $OCl^-$ are the three possible forms of free total chlorine:

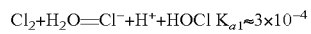

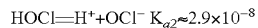

As can be seen in the above equations, chlorine generation occurs in the presence of an excess of $Cl^-$. Furthermore, the amount of the three forms of free total chlorine as a function of pH and $Cl^-$ can be determined algebraically by using the above described equilibria as follows:

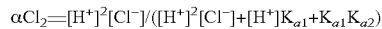

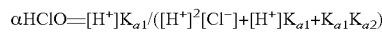

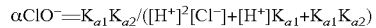

Figure 3:
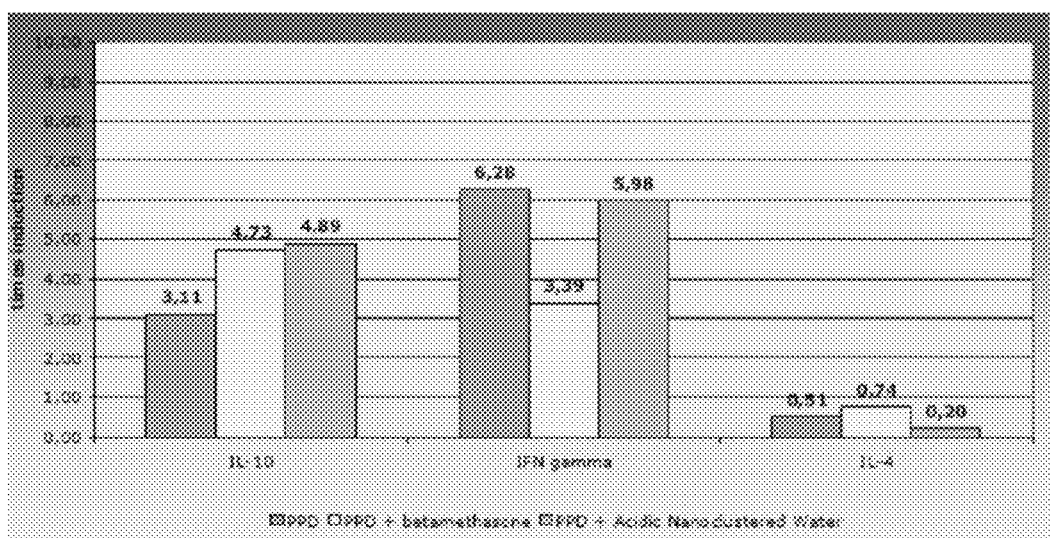
FIG. 3 is a graph illustrating the modulation of the immune system cytokines by Acidic Nanoclustered Water.
Figure 4:
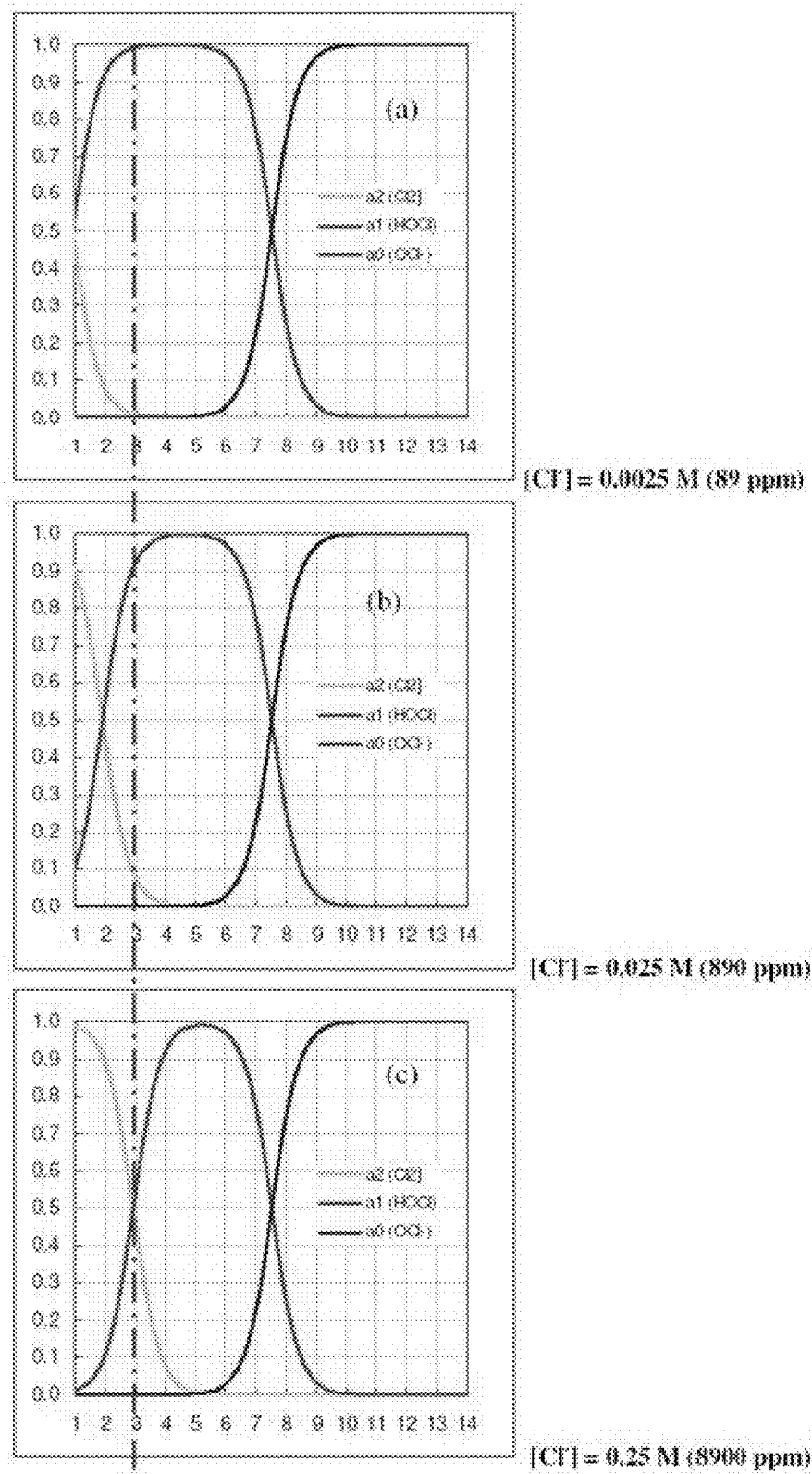
FIG. 4 is a set of graphs illustrating the concentration of various chlorine species as a function of pH.

These equations can be used to simulate the chlorine concentration at different pH values. For example, FIG. 3 is a graphical simulation of the concentration of various chlorine species as a function of pH. As can be seen in FIG. 3, at a typical pH for the water of 2.8-3.0 (indicated by the green dash-and-dotted line), free chlorine is predominantly present as $Cl_2$ and HClO, and the relative amount of the two species is strongly affected by the amount of chlorides, and increase of which results in an increase of the amount of chlorine gas with respect to HClO.

It is generally recognized that diluted hypochlorous acid solutions are unstable due to decomposition. This decomposition can occur according to a first pathway:

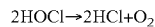

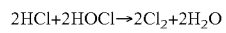

Or as according to a second pathway, in which chlorous acid ($HClO_2$) is an intermediate in the formation of chloric acid ($HClO_3$):

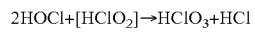

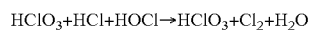

Kinetic studies have indicated that both decomposition pathways are pH dependant and increase with concentration, temperature, and exposure to light. Furthermore, the first process can be accelerated by catalysts, and the second process can be accelerated in the presence of other electrolytes, notably chloride ions. Due to decomposition, hypochlorite solutions can be more stable than hypochlorous acid solutions. For this reason, commercial solutions often have neutral or alkaline pH, which causes the free chlorine to exist as hypochlorite and not hypochlorous acid.

Although one does not intend to be bound to any particular theory, it is believed that the low chloride ion content is one of the main reasons for the unusual and advantageous stability over time of the electrolytic acid water, both to evaporation and self decomposition. Preferably, the amount of chlorides both at the beginning and at the end of the electrolytic process is low (200 ppm or lower), so that the water comprises chlorine in the form of HClO. For example, in a particular embodiment, the water can comprise ~50 ppm of free chlorine, and ~200 ppm of chloride ions. At pH 2.80, this corresponds to 99.3% HClO, and 0.7% dissolved gaseous chlorine.

The conductivity of the water preferably ranges from 900 to 1800 uS/cm, and more preferably ranges from 1000, 1100, 1200, or 1300 to 1400, 1500, 1600, or 1700 uS/cm. The free chlorine content of the water preferably ranges from 20 to 80 ppm, more preferably ranges from 30 or 40 to 60 or 70 ppm, and most preferably is about 50 ppm. The chloride ion content of the water preferably ranges from 150 to 250 ppm, more preferably ranges from 160, 170, 180 or 190 to 210, 220, 230, or 240 ppm, and most preferably is about 200 ppm. The chlorite content of the water preferably ranges from 50 to 150 ppb, more preferably ranges from 60, 70, 80 or 90 to 110, 120, 130, or 140 ppb, and most preferably is about 100 ppb. The chlorate content of the water preferably ranges from 0.5 to 1.5 ppm, more preferably ranges from 0.6, 0.7, 0.8, or 0.9 to 1.1, 1.2, 1.3, or 1.4 ppb, and most preferably is about 1 ppm.

Due to its chemical composition and acidity, the free chlorine in the water can be present in the form of hypochlorous acid (HOCl) and chlorine gas ($Cl_2$). The relative amount of HOCl and $Cl_2$ in the water preferably ranges from 99.9% HOCl and 0.1% $Cl_2$ to 95% HOCl to 5% $Cl_2$, more preferably ranges from 99.5% HOCl and 0.5% $Cl_2$ to 98.5% HOCl to 1.5% $Cl_2$, and most preferably is about 99.3% HOCl and 0.7% $Cl_2$.

Because the free chlorine in the water is present in the form of HOCl and $Cl_2$ in the ranges described above, the water can be highly stable against both evaporation and self decomposition. In an exposed, non-agitated state at a temperature of 25° C., the water preferably maintains a level of chlorine for a time of 2, 3, 4, 5, 6, 7, 8, 9, or 10 days. In an exposed, agitated state at a temperature of 25° C., the water preferably maintains a level of chlorine for a time of 8, 12, 16, 20, or 24 hours. In a closed state at a temperature of 25° C., the water preferably maintains about 90% of the free chlorine after a time of 3 months, and about 85% of the free chlorine after a time of 12 months. In a closed state at a temperature of 30° C., the water preferably maintains about 90% of the free chlorine after a time of 3 months, and about 80% of the free chlorine after a time of 12 months. In a closed state at a temperature of 40° C., the water preferably maintains about 90% of the free chlorine after a time of 3 months, and about 85% of the free chlorine after a time of 12 months.

Making Electrolytic Acid Water

The electrolytic acid water can be prepared, for example, by using the methods and electrolysis devices described in PCT Publications WO 2008/131936 and WO 2007/048772. The contents of said applications are hereby incorporated by reference as if fully set forth herein.

Referring now to FIG. 1, the electrolysis device can comprise an electrolysis chamber 3 divided into two portions by a membrane 4, and a pair of electrodes 1 and 2 within said chamber.

Preferably, both electrodes of the device are nano-coated electrodes as defined below. However, the advantages in terms of low cost and efficiency of the electrolysis process, as well as the advantages in terms of water stability over time, can be obtained also if only one of the two electrodes is nano-coated as defined above.

Preferably, the device according to the invention also comprises a membrane 4 adapted to divide the at least one chamber into two half-chambers, wherein the half-chamber that contains the anode is termed an anode half-chamber, and the half-chamber that contains the cathode is termed a cathode half-chamber. The membrane is advantageously an ultrafiltration membrane which can occupy the chamber partially or totally.

The membrane 4 can be of the type used in conventional electrolytic cells, but is preferably based on size exclusion technology at the nano-scale. Preferably, the membrane is made of ceramic material with open porosity, coated with metallic nano-particles, preferably nano-particles of oxides of zirconium, yttrium, aluminum or mixtures thereof. The metallic nano-particles used to make the coating are preferably in powder form. As regards the size distribution within the powder, preferably an amount at least equal to 70%, 75%, or 80% by weight of the particles that are present in the powder, more preferably at least equal to 85%, have a particle diameter ranging from 30 to 100 nm, 40 to 70 nm, or 50 to 60 nm.

By resorting to nanometer particles to manufacture the membrane 4, the average pore size of the final membrane has been found to be extremely constant over time and adaptable according to the requirements of how the water is to be processed. Preferably, the average pore size is from about 120 to about 180 nm (mean or median). Size constancy over time and constancy of the pore dimensions themselves are two aspects which differentiate the ceramic membrane described here from the textile membranes conventionally used in equivalent devices (which are instead subject to rapid deterioration over time). It is preferred that at least 50%, 70%, 90%, 95%, 98% or 99% of the pores have a diameter between 120 and 180 nm. These aspects have shown a positive effect on the stability of the water obtained after electrolysis, where this effect combines with, and augments, the stabilizing effect produced by the use of an electrode as defined above.

Importantly, the nano-sized dimensional features of the membrane and electrodes enhance the amount of active surface per unit of geometric surface, which creates a high apparent current density (i.e. the current intensity per unit of geometric surface). As a result, a high current intensity (ampere) and electric potential (voltage) can be provided to the solution, which can impart unique chemical and biological characteristics to the water. Preferably, the water is produced by applying a current intensity in the range of about 100 to about 39 ampere (24 to 18 volt) to a diluted sodium chloride solution in deionized water. By applying the high current intensity, a chemical composition of a low chloride ion content, low chlorite and chlorate content, and high hypochlorous acid content can be achieved.

The amount of current applied to the water preferably ranges from 30 to 120 ampere, more preferably ranges from 40, 50 or 60 ampere to 90, 100, or 110 ampere, and most preferably is about 80 ampere. The amount of voltage applied to the water preferably ranges from 15 to 35 volt, more preferably ranges from 16, 17, or 18 volt to 22, 23, or 24 volt, and most preferably is about 20 volt.

In a preferred electrolysis device, each half-chamber is connected to the outside of the device through:
openings 7 and 8 arranged in the upper part of the half-chamber from which the water to be subjected to electrolysis is inserted, and
additional openings 5 and 6 arranged in the lower part of the half-chamber which can act as a discharge for the resulting acid and alkaline fractions (referenced as "acid water" and "alkalescent water" in FIG. 1). The second opening on the lower part of each half chamber is provided with closure means (not shown) which is adapted to prevent the water that has not yet separated from leaving the half-chamber and are adapted to be opened at the end of the electrolytic process.

With specific reference to FIG. 1, the operating mechanism of a device as described above provided with all the essential and optional elements that have been listed, therefore entails treating water by introducing it from above, by means of the water input ducts, into the two half-chambers of the main chamber. Here, the water, under the action of the cathode and of the anode previously connected to the negative and positive poles of an electric voltage source, is split into positive and negative ions, which, as is known, are attracted by the respective opposite poles. In passing from one half-chamber to the other, the nano-porous membrane acts as a filter for said ions and for any charged particles, allowing only the particles of sufficiently small size to pass.

The water input to the unit can be characterized by its conductivity, preferably measured in μS/cm. Thus, for example, the water can be described by the consistency of conductivity in the water input. For example, the conductivity should vary by no more than 50, 20, 10, 5 or even 2 μS/cm, or 100, 50, 20 or 10%. The water may also be described by the conductivity of the water itself. The conductivity can range from 0.5, 1.0 or 1.5 μS/cm to 50, 25, 10, 5 or even 3 μS/cm, based on any selection of endpoints. The conductivity preferably ranges from 0.5 to 10 or 0.5 to 3 μS/cm, and the most preferred conductivity is about 2 μS/cm. It has been discovered that by controlling the consistency of the conductivity, and by lowering the conductivity to the preferred values, one is able to obtain much more consistent quality electrolyzed water, with a consequent reduction in NMR half line width. Suitable types of water for input into the unit include reverse osmosis water, deionized water, and distilled water. A preferred type of water due to its constant conductivity is osmotic water prepared by reverse osmosis.

The water preferably contains sodium chloride, or some other alkali metal salt, to facilitate the electrolysis. The sodium chloride is preferably pharmaceutical grade. The quantity of sodium chloride contained in the water is such that the water obtains a specific level of conductivity. The conductivity of the input solution preferably ranges from 50 μS/cm to 100 μS/cm, more preferably ranges from 150 μS/cm to 200 μS/cm, and most preferably is about 200 μS/cm.

Also of importance, the filter prevents the transmission of heavy metals from one chamber to the other. Thus, by introducing the water into the acidic or alkaline chamber, one is able to produce alkaline or acid water having practically no contamination by metallic radicals (or at least beyond the limits of detection).

A method of using such a unit for making electrolytic acid water having a NMR half line width using $^{17}$O-NMR of from about 45 to less than 51 Hz comprises:

(a) providing an electrolysis unit comprising: (i) a cathode chamber, an anode chamber, and a filter separating said chambers (preferably characterized by a porosity that allows ionized fractions of nano-clustered $H_2O$ to pass, such as when the porosity is predominantly characterized by pores of from about 120 to about 180 nm in diameter (preferably having a mean diameter between 120 and 180 nm)); and (ii) a cathode situated in said cathode chamber and an anode situated within said anode chamber, wherein at least one of said anode and cathode is coated by a residue of particles in which greater than 70% by weight of said particles have a diameter of from 40 to 100 nm;

(b) introducing a solution of water and an alkali metal into one or both of said chambers; and (c) applying an electric potential to said anode and said cathode, for a time and to an extent sufficient to produce electrolyzed acidic water having a NMR half line width using $^{17}$O of from about 45 to less than 51 Hz.

Electrode Construction

Referring again to FIG. 1, the electrolysis device includes electrodes 1 and 2 that comprise a surface coating which comprises nano-particles of one or more metals. Preferably, the electrodes comprise a core which is made of a metallic material, a nonmetallic material or combinations thereof.

If the core is made of metallic material, it can be made for example of an alloy of titanium and platinum or an alloy of steel and graphite. If the core is made of a nonmetallic material, it can be made for example of graphite. The core may also comprise different layers, such as for example a core made of graphite which is coated with an outer layer of metal, for example titanium. The term "metal" references both a metal and chemical compounds which comprise said metal, such as its oxides. A preferred core is made of $TiO_2$.

The electrode can be characterized with respect to known electrodes substantially due to the presence of a nanometer covering (hereinafter also referenced as coating) which is extremely smooth, i.e., a layer for covering the core which includes metallic nano-particles.

The metals of which the nano-particles of the coating are made are selected preferably among one or more of titanium, iridium, yttrium, ruthenium, zinc, zirconium platinum, selenium, tantalum and compounds thereof. Preferred metal compounds are oxides of the mentioned metals. A preferred coating comprises $ZrO_2$, $ZnO$, $Ru_2O_3$, $IrO_2$ and $Y_2O_3$, or $TiO_2$, $Pt/ZrO_2$, $SnO_2$, $Ta_2O_5$, and $IrO_2$. Preferably, the various metals are used in powder form.

The coating can also comprise a nonmetallic carrier material, for example particles of one or more polymers. The polymer can be synthetic (such as for example plastics, acrylic polymers, et cetera) or partly synthetic (such as for example modified celluloses, modified starches, et cetera). The metallic nano-particles comprised within the coating are preferably used in powder form. As regards the size distribution within the powder, preferably an amount at least equal to 70%, 75%, or 80% by weight of the particles that are present in the powder, more preferably at least equal to 85%, has a particle diameter ranging from 40 to 100 nm, 50 to 90 nm, or 60 to 80 nm.

The electrode coating can be provided by means of nanotechnology techniques which are known to a person skilled in the art and are adapted to produce a smooth surface, for example by sintering the powder or the mixtures of metallic nano-powders.

The individual metals in powder form can be applied to the electrode so as to produce the coating: 1) as a preformed mixture, and/or 2) in the form of discrete layers which are applied sequentially and mutually superimposed and wherein each layer consists of a single metal, and/or 3) in the form of discrete layers which are applied sequentially and mutually superimposed and in which each layer consists of two or more metals but not simultaneously of all the metals that are present in the coating.

Preferably, the method comprises the step (A) of preparing the coating of the electrode by sintering powders of nano-particles of one or more metals as defined above directly on the core of the electrode. Preferably, step (A) comprises the following steps to be performed in the order in which they are listed here:

(A1) preparing one or more powders of metallic nano-particles as defined above, (A2) dissolving the one or more powders of nano-particles in a suitable solvent and in at least such a quantity as to be able to dissolve all the powder to be applied, obtaining one or more solutions, and (A3) sintering the one or more solutions obtained in the preceding step on a metal plate, preferably passivated on its surface, which will form the core of the electrode.

Preferably:

the one or more powders of metallic nano-particles of step (A1) is a combination of powders of $ZrO_2$, ZnO, $Ru_2O_3$, $IrO_2$ and $Y_2O_3$, or $TiO_2$, $Pt/ZrO_2$, $SnO_2$, $Ta_2O_5$, and $IrO_2$, advantageously obtained by hydrothermal chemical processing, at least 70%, 75%, or 80% and more preferably at least 85% by weight of the particles in the powder have a diameter ranging from 60 to 80 nm;

the solvent of step (A2) in which each powder is dissolved is preferably a 30% solution by weight of hydrochloric acid in water, in at least such an amount as to be able to dissolve all the powder to be applied, step (A3) consists in sintering the aqueous solutions of hydrochloric acid obtained from step A(2) on both faces of a $TiO_2$ plate which is passivated on its surface and has a thickness ranging from 0.15 to 0.35 mm, wherein sintering may occur according to the steps listed below in Table 2:

TABLE 2

Sintering Steps

| Step | Solution | Dosage per unit surface | Sintering time(min) | Sintering temperature(° C.) |
|---|---|---|---|---|
| 1 | $IrO_2$ | 0.2 g/m² | 45 | 450 |
| 2 | $Ru_2O_3$ | 0.2 g/m² | 45 | 450 |
| 3 | $ZnO + Y_2O_3$ (Y at 2 mol) | 0.15 g/m | 60 | 550 |
| 4 | $IrO_2$ | 0.25 g/m² | 45 | 450 |
| 5 | $Ru_2O_3$ | 0.25 g/m² | 60 | 550 |
| 6 | $ZrO_2 + Y_2O_3$ (Y at 3 mol) | 0.1 g/m² | 60 | 550 |
| 7 | $Ru_2O_3$ | 0.15 g/m² | 60 | 550 |
| 8 | $IrO_2$ | 0.15 g/m² | 60 | 550 |
| 9 | $IrO_2 + Ru_2O_3$ | 0.15 g/m² + 0.15 g/m² | 60 | 600 |
| 10 | $ZrO_2 + Y_2O_3$ (Y at 3 mol) | 0.1 g/m | 60 | 600 |
| 11 | $IrO_2 + Ru_2O_3$ | 0.15 g/m² + 0.15 g/m² | 60 | 600 |

Resorting to multiple sintering steps has been found to be particularly useful in order to eliminate any roughness from the surface of the electrode and obtain an extremely hard and smooth surface. An electrode as defined above, used as part of a device for providing the electrolysis of water, produces the following advantages:

more efficient electrolysis, in that there is a lower consumption of salts such as NaCl, used conventionally to accelerate the electrolysis of low-conductivity fluids such as water; and if both electrodes are electrodes according to the invention, the possibility to provide a continuous change of polarity of the electrodes ("polarity swapping"). The sudden change of polarity allows the charged particles that are present in the fluid subjected to electrolysis to circulate in both directions instead of just in one (forced by the charge of the particles and by the unchangeable sign of the electrodes), thus avoiding the forming of deposit-producing masses at the level of the electrodes and thus keeping their surface clean and their efficiency at the maximum level. Moreover, if a semipermeable membrane is provided within the electrolytic cell and divides the two anode and cathode half-chambers, the change of polarity avoids the clogging of the pores of said membrane, extending the life of the device;

the presence of a nanometer coating determines an accumulation of charge by the upper electrode to more than 100% with respect to conventional electrodes. This allows to provide a qualitatively and quantitatively different electrolysis at significantly higher potentials, with the effect of, for example, reducing the size of molecular clusters;

the obtainment of a very high consistency, smoothness and surface density, aspects which avoid the solubilization of the electrode itself or the forming of sediments on its surface, which would then occur in the acid and alkaline water fractions. The same aspects are also the basis for the substantially nil release of heavy metals and other compounds which constitute the surface and core of the electrode within the acid and alkaline water fractions. As will be mentioned also hereafter, the absence of heavy metals in the water leads to an amazing stability thereof over time, with preservation of characteristics such as ORP, pH and molecular cluster size. This stability is unknown to known equivalent products. The same aspects are also the basis for the minimal maintenance required by the electrode, which can be changed with a significantly lower frequency than known electrodes, reducing costs and increasing ease of production;

the possibility to obtain quantum effects (known in the literature also by the term "nano-effects") by means of the nanometer dimensions of the coating particles. Briefly, when nanometer dimensions are reached, the optical, magnetic and electrical properties of matter change radically. By reducing the dimensions until the typical nanometer dimensions of so-called clusters are reached, due to the small number of atoms that are present in said cluster and to its reduced volume, a discretization of the energy levels (quantization) becomes apparent in the electron structure and depends on the size of the cluster, this phenomenon is known as "quantum size effect" and entirely new characteristics, which contrast with the ones that are typical of the material at ordinary dimensions, depend from it. In the present case, the best performance has been obtained with powders which have a size distribution centered in an interval ranging from 60 to 80 nm as indicated above. As a whole, the effects described above produce the simultaneous presence of three factors: stability of the resulting water, ease of its production (for example thanks to the lower maintenance costs and to the greater durability of the device as a whole) and an increase in its quality (especially in terms of purity and constancy of properties over time). In particular, the increase in the quality of the water can be measured both in terms of uniformity of the dimensions of the molecular clusters (higher percentage of micromolecules with respect to the number of macromolecular clusters) and in terms of increased stability over time of the properties given to the water by the electrolysis itself (above all pH, ORP and cluster size). The stability increase presumably achieves the preservation over time of the structural surface characteristics of the electrodes coated with a nano-coating as described here.

EXAMPLES

Example 1

Objective

Determine the efficacy of acidic nanoclustered water (ANW) against several strains of bacteria, viruses and fungi.

Bacterial Activity

Bacterial activity was assessed with the method of UNI (Italian Organization for Standardization) EN 1040 (quantitative suspension test for the evaluation of basic bactericidal activity of chemical disinfectants and antiseptics). According to this method, a substance is classified as bactericidal for a specific microorganism if it reduces the bacterial count by at least 5-$\log_{10}$ following 5 minutes of contact at 20° C. ANW solutions at three different concentrations (80%, 50%, and 25%) were tested against two strains of bacteria known to cause eye infections, Staphylococcus aureus (ATCC 6538) and Pseudomonas aeruginosa (ATCC 15442). Table 3 below shows the antibacterial effect of the three different concentrations of ANW, with viability reduction values expressed as the $\log_{10}$ reduction.

TABLE 3

Antibacterial Effect of ANW

| Species | Solution | Viability Reduction | | |
| --- | --- | --- | --- | --- |
| | | 80% | 50% | 25% |
| Staphylococcus aureus (ATCC 6538) | ANW | >5.41 | >5.41 | 5.35 |
| Pseudomonas aeruginosa (ATCC 15442) | ANW | >5.48 | <4.10 | <4.10 |

As shown in Table 3, ANW can be classified to be a bactericidal against both strains at a concentration of 80%.

Bacterial activity was also assessed against the same two strains of bacteria in the presence of 5% of human blood in the medium as organic soil interference. Viability reduction was assessed after 10, 30, 60 and 120 minutes of exposure to pure ANW at 31° C. Table 4 below shows the antibacterial effect of the pure ANW at each time point, with viability reduction values expressed as the $\log_{10}$ reduction.

TABLE 4

Antibacterial Effect of ANW in Presence of 5% Human Blood

| Species | Solution | Viability Reduction | | | |
| --- | --- | --- | --- | --- | --- |
| | | 10 min | 30 min | 60 min | 120 min |
| Staphylococcus aureus (ATCC 6538) | ANW | >5.6 | >5.6 | >5.6 | >5.6 |
| Pseudomonas aeruginosa (ATCC 15442) | ANW | >5.6 | >5.6 | >5.6 | >5.6 |

As shown in Table 4, pure ANW was demonstrated to have a bactericidal effect against both strains at the lowest tested time point of 10 minutes.

Bacterial activity was also assessed against Propionibacterium acnes bacteria in the presence of 1% fetal bovine serum in the medium as organic soil interference. Viability reduction was assessed after 1, 5, 15 and 30 minutes of exposure to pure ANW at 31° C. Table 5 below shows the antibacterial effect of the pure ANW at each time point, with viability reduction values expressed as the $\log_{10}$ reduction.

TABLE 5

Antibacterial Effect of ANW in Presence of 1% Fetal Bovine Serum

| Species | Solution | Viability Reduction | | | |
| --- | --- | --- | --- | --- | --- |
| | | 1 min | 5 min | 15 min | 30 min |
| Propionibacterium acnes (ATCC 11827) | ANW | >6.9 | >6.9 | 5.3 | >6.9 |

As shown in Table 5, pure ANW was demonstrated to have a bactericidal effect at the lowest tested time point of 1 minute.

Fungal Activity

Fungal activity was assessed with the method of UNI EN 1275 (quantitative suspension test for the evaluation of basic fungicidal activity of chemical disinfectants and antiseptics). According to this method, a substance is classified as fungicidal for a specific microorganism if it reduces the fungi count by at least 4-$\log_{10}$ following 15 minutes of contact at 20° C. ANW solutions at three different concentrations (80%, 50%, and 25%) were tested against two strains of fungus known to cause infections, Candida albicans (ATCC 10231) and Aspergillus niger (ATCC 16404). Table 6 below shows the antifungal effect of the three different concentrations of ANW, with viability reduction values expressed as the $\log_{10}$ reduction.

TABLE 6

Antifungal Effect of ANW

| Species | Solution | Viability Reduction | | |
| --- | --- | --- | --- | --- |
| | | 80% | 50% | 25% |
| Candida albicans (ATCC 10231) | ANW | >4.37 | <3.09 | <3.09 |
| Aspergillus niger (ATCC 16404) | ANW | <3.12 | <3.12 | <3.12 |

As shown in Table 6, ANW can be classified to be a bactericidal against Candida albicans (ATCC 10231) at a concentration of 80%.

Viral Activity

Viral activity was assessed against Human Immunodeficiency Virus type 1 (HIV-1), Herpes Simplex Virus type 1

(HSV-1), and Herpes Simplex Virus type 2 (HSV-2) in the presence of 5% fetal bovine serum in the medium as organic soil interference. For HIV-1, viability reduction was assessed after 10 minutes of exposure to pure ANW at 21.5° C. For HSV-1 and HSV-2, viability reduction was assessed after 5 minutes of exposure to pure ANW at 35° C. Table 7 below shows the antiviral effect of the pure ANW on each virus, with viability reduction values expressed as the $\log_{10}$ reduction.

TABLE 7

Antiviral Effect of ANW

| Species | Solution | Exposure | Viability Reduction |
|---|---|---|---|
| HIV-1 (strain HTLV-III$_b$) | ANW | 10 min at 21.5° C. | >4.5 |
| HSV-1 (ATCC VR733) | ANW | 5 min at 35° C. | <5.5 |
| HSV-2 (ATCC VR734) | ANW | 5 min at 35° C. | 4.25 |

As shown in Table 7, ANW can inactivate the tested viruses.

Example 2

Objective

Determine the efficacy of acidic nanoclustered water (ANW) at promoting corneal healing and cataract healing.

Corneal Ulceration Healing

Corneal healing activity was assessed in an in vivo rabbit model. Corneal eye wounds were experimentally provoked in 8 rabbits. The left and right eyes were then treated with ANW and saline, respectively, by applying 100 µl of the solutions 4 times per day for 14 consecutive days. On the $4^{th}$, $9^{th}$, and $14^{th}$ day after the surgery, images of each wound were taken under a slit lamp microscope and the area of each wound was calculated with the software Topcon IMAGENET 2000. The wound area was then used to calculate the wound healing rate (WHR) using the following equation:

WHR=100(1−(wound area at timing point)/(initial wound area))

Table 8 below shows the Wound Healing Rate of ANW and saline treated eyes at 4, 9, and 14 days.

TABLE 8

Corneal Ulceration Healing Effect of ANW and Saline

| | Wound Healing Rate (WHR) | | |
|---|---|---|---|
| | Day 4 | Day 9 | Day 14 |
| ANW | 77.78 ± 9.06 | 83.32 ± 12.23 | 87.20 ± 13.16 |
| Saline | 71.84 ± 19.38 | 63.45 ± 23.02 | 64.23 ± 28.28 |
| T-value | 1.36 | 3.73 | 3.61 |
| P-value | >0.05 | <0.05 | <0.05 |

As shown in Table 8, ANW was significantly more effective than saline in corneal ulcer healing at the latter two of the three time points.

The wounds were also observed daily for the presence of wound closure. On day 14, it was observed that half of the corneal ulcers treated with ANW were healed, while some corneas treated with saline were still presenting a large ulcer. Exemplary photographs (not shown) were taken of the corneal wounds in 3 of the rabbits on day 14.

The wounds were also observed daily for the presence of infections and inflammation. ANW was observed to reduce inflammation after injury. Furthermore, two of the eyes treated with saline were seriously infected with hypopyon, and the inflammation of these corneas was too intensive to identify the pupil. Exemplary photographs and histological images (not shown) were obtained of the inflammation in 2 of the rabbits.

Histological evaluation also was used to observe regeneration of the cornea and scarring. ANW was observed to increase regeneration and reduce scarring as compared to saline. Furthermore, epithelium deficiency was observed in all of the eyes treated with saline, and none of the eyes treated with ANW. Histological images (not shown) depicting scarring of cornea wounds were taken in 3 of the rabbits.

The wounds were also observed for the presence of angiogenesis. Neovascularization was observed in 35% of the corneas treated with saline, and none of the eyes treated with ANW. Exemplary photographs (not shown) depicting angiogenesis were taken of 2 of the rabbits.

Cataract Healing

Cataract healing activity was assessed in an in vivo rat model. Cataract was induced by intraperitoneal injection of d-galactose in 1 rat at a dose of 10 g/kg per day (twice/day). The left and right eyes were then treated with ANW and saline, respectively, by applying 1 drop of the solutions 4 times per day for 30 consecutive days. On day 30, it was observed that the cataract treated with ANW was significantly healed as compared to the cataract treated with saline. Photographs (not shown) depicting the cataracts were taken on day 30.

Example 3

Objective

Determine the safety of acidic nanoclustered water (ANW) in systemic and topical applications.

In Vitro Studies

Citotoxicity was assessed with the method of ISO (International Organization for Standardization) 10993-5. According to this method, a substance is classified based on its effect on a cell culture. 100 µl of pure ANW was applied to a cell culture of murine fibroblasts L-929 and the cells were evaluated after 24 hours of incubation at 37° C. Some malformed cells were observed after the period of incubation. Based on these results, ANW was defined as "slightly cytotoxic" (grade 1 of 4).

Mutagenicity was assessed with the method of OECD 471. According to this method, a substance is classified based on its ability to induce point mutations in bacteria. Five mutant strains of *Salmonella typhimurium* (TA 1535, TA 1537, TA 98, TA 100, and TA 102) were studied both in the presence and in the absence of ANW. Based on the results of a reverse mutation assay (Ames' test), the substance ANW was defined as non mutagenic.

Systemic Toxicity Studies

Acute toxicity was assessed with the method of ISO 10993-11, 2006, Biological Evaluation of Medical Devices—Part 11: Tests for Systemic Toxicity. According to this method, a substance is classified not toxic if animals injected with the substance do not show a significantly greater biological reaction than animals treated with a control article. 10 female Swiss albino mice were injected by intraperitoneal route with either ANW or saline in the amount of 50 mL/kg. The animals were observed for clinical signs immediately after injection, and at 4, 24, 48, and 72±2 hours after injection. ANW did not induce a significantly greater biological reaction than the control, and was therefore classified as not toxic.

Skin Irritation Studies

Dermal irritation following acute exposures was assessed with the method of ISO 10993-10. 0.5 mL of pure ANW was applied with a patch on the shaved skin of three male albino rabbits. The patch was held on the skin by means of a non-irritating adhesive plaster for 4 hours. The skin reaction was observed upon removal of the patch and 24, 48, and 72 hours after removal. No sign of either erythema or edema was observed. Based on these results, ANW was determined to be non-irritating for skin, which a Skin Irritation Index of 0.00.

Dermal irritation following repeated exposure also was assessed with the method of ISO 10993-10. Three male New Zealand rabbits were treated 5 days a week for 4 weeks with two consecutive daily administrations of 5 mL of pure ANW or saline as a control applied with a patch for one hour. The skin reaction was before and after each application throughout the entire 4 week period. No sign of either erythema or edema was observed. Furthermore, upon sacrifice, no signs of inflammation were detected in histological images. Based on these results, ANW was determined to not exhibit any significant irritancy in the skin.

Skin Sensitization Studies

Delayed-type skin hypersensitivity was assessed with the method of ISO 10993-10: Guinea-Pig Maximization test. The test used 15 albino female Hartley guinea pigs (10 treated and 5 control). The injection phase (Day 0) was carried out by administering three 0.1 mL intradermal injections to each animal: (a) complete Freund's adjuvant, (b) either pure ANW (test) or saline (control), (c) either ANW (test) or saline (control) mixed together with complete Freund's adjuvant. A skin massage with 1 mL SLS 10% was then performed on Day 6. The induction phase (Day 7) was carried out by applying 1 mL of either the test or the control, left in place for 48 hours with an occlusive patch. The challenge was carried out on Day 21 through the application to each animal (both treated and control) of dressings with of 1 mL of ANW on the right side and 1 mL of saline on the left side, left in place for 24 hours.

Assessments were carried out on the 23rd day (24 hours after patch and removal) and on the 24th day (48 hours after patch and removal). The intensity of erythema and/or edema was evaluated according to the Magnusson and Kligman scale from 0 to 3.

No abnormalities were observed in either the treated or the control animals. Based on these results, ANW was determined to not exhibit delayed contact dermatitis potential.

Ocular Irritation Studies

Ocular irritation was assessed with the method of ISO 10993-10. In a first experiment, three New Zealand white rabbits were treated by instilling 0.1 mL of pure ANW into the left eye, leaving the right eye untreated as a control. The eyes were examined 1, 24, 48 and 72 hours after instillation through fluorescein staining and slit-lamp observation. No signs of irritation were observed in any of the eyes. Based on these results, ANW was determined to be a non-irritant for the ocular tissue of New Zealand White rabbits.

In a second experiment, ocular irritation was again assessed with the method of ISO 10993-10. Three New Zealand white rabbits were treated by instilling 0.1 mL of pure ANW into the left eye as a test, and instilling 0.1 mL of NaCl containing water (saline) into the right eye as a control. The treatment was repeated for 30 consecutive days. No signs of irritation were observed in any of the test or control eyes at any of the observation points. Based on these results, the test article ANW was determined to be a non-irritant for the ocular tissue of New Zealand White rabbits.

Summary of Toxicology Studies

Table 9 below shows a synopsis of the safety studies reported above in Example 3.

TABLE 9

Synopsis of ANW Safety Studies

| Effect | Method | Results |
|---|---|---|
| Cytotoxicity | In vitro mouse fibroblasts L-929 | Slightly cytotoxic (grade 1 of 4) |
| Acute Skin Irritation | Acute exposure in rabbits | Non-irritant |
| Repeated Skin Irritation | Repeated exposure in rabbits | Non-irritant |
| Delayed hypersensitivity | Maximisation test in guinea pigs | Non-sensitising |
| Primary ocular irritation | Acute administration in rabbits | Non-irritant |
| Repeated ocular irritation | Repeated administration in rabbits | Non-irritant |
| Genotoxicity | Ames test | Non-mutagenic |
| Acute Systemic Toxicity | i.p. dosing in mice | Not toxic up to 50 mL/kg i.p. |

Example 4

Objective

Determine the efficacy of acidic nanoclustered water (ANW) for modulating the activity of the immune system In Vitro Study of PBMC Proliferation The ability of ANW to inhibit the proliferation of peripheral blood mononuclear cells (PBMC) was assessed in an in vitro cellular model using 12 batches of PBMC. In the experiment, 4 of the batches were exposed to betamethasone (10 nM), a glucocorticoid steroid with anti-inflammatory and immunosuppressive properties, 4 of the batches were exposed to a 1:10 dilution of ANW, and the remaining 4 batches were exposed to a 1:20 dilution of ANW. Table 10 below shows the inhibition effect that was measured for each of the 12 batches.

TABLE 10

Inhibition of PBMC Proliferation

| | Batch 1 | Batch 2 | Batch 3 | Batch 4 | Mean |
|---|---|---|---|---|---|
| Betamethasone (10 nM) | 87.7% | 85.7% | 79.4% | 88.5% | 85.3% |
| Acidic Nanoclustered Water (1:10) | 39.9% | 29.0% | 19.3% | 16.6% | 26.2% |
| Acidic Nanoclustered Water (1:20) | 17.3% | 22.0% | 4.0% | 7.0% | 12.6% |

As shown in Table 10, ANW inhibited PBMC proliferation at both dilutions. These dilutions have previously been shown to not be significantly toxic on this cell type in vitro.

In Vitro Study of T-Cell Activation

The ability of ANW to modulate immunoregulatory cytokines was assessed in an in vitro cellular model using PBMC from 4 blood donors stimulated with purified protein derivatives from *Mycobacterium tuberculosis* (PPD), a prototypical Th1 antigen. In the experiment, batches of PBMC cells were stimulated with PPD alone, PPD plus betamethasone (10 nM), and PPD plus Acidic Nanoclustered Water (1:10 dilution). T-Cell activation was measured by testing levels of three cytokines: IL-10 (expressed in T-Cells), IFN-gamma (expressed in Th-1 cells), and IL-4 (expressed in Th-2 cells). FIG. 3 shows the levels of each cytokine as compared to non-stimulated PBMC.

As shown in FIG. 3, ANW up-regulated IL-10 production by stimulated PMBC in a statistically significant way (T test: $p<0.05$). Interleukin IL-10 is an important immunoregulatory cytokine. Its main biological function is to limit and terminate inflammatory responses, and to regulate the differentiation and proliferation of several immune cells. IL-10 deficiency is regarded as pathophysiologically relevant in inflammatory disorders characterized by a type 1 cytokine pattern such as psoriasis. Thus, the immune-modulating properties of ANW and, specifically, the IL-10 activating properties of ANW, suggest than ANW can be used as a direct therapeutic agent for several skin diseases.

Example 5

Objective

Compare the stability of acidic nanoclustered water (ANW) with the reported stability of other electrolyzed waters of similar pH, ORP, and composition.

Comparison of ANW with Electrolyzed Oxidizing (EO) Water of Soo-Voo Len

The stability of ANW in open and closed conditions at 25° C. was compared with the stability of EO water as reported in the article "*Effects of Storage Conditions and pH on Chlorine Loss in Electrolyzed Oxidizing (EO) Water*"—Journal of Agricultural and Food Chemistry—2002, 50, 209-212 by Soo-Voon Len, et al.

In Soo-Voo Len, electrolyzed water with an acidic pH (2.5-2.6), OPR>1000 mV (1020-1120), and a free chlorine content ~50 ppm (53-56 ppm) was generated with an ROX-20TA device manufactured by Hoshizaki Electric Inc. (Aichi, Japan) using a current intensity of 14 Ampere and 7.4 Volt.

The article reports that in an open condition at 25° C., the chlorine in the electrolyzed water was completely lost after 30 hours when agitated, and after 100 hours when not agitated. Furthermore, as seen in FIG. 1 of the article, the free chlorine was almost completely lost after 10 hours in open, agitated, diffused light conditions. The article also reports that in a closed dark condition at 25° C., the free chlorine in the electrolyzed water decreased by approximately 40% after 1400 hours (about 2 months).

In comparison, ANW stored in an open condition at 25° C. without agitation completely lost chlorine after 240 hours (10 days), more than twice as long as the EO water in Soo-Voo Len (100 hours). Furthermore, ANW stored in an open condition at 25° C. with agitation and light completely lost chlorine after 24 hours, more than twice as long as the EO water in Soo-Voo Len (10 hours). Finally, ANW stored in a closed condition at 25° C. lost 8.44% of free chlorine after 3 months, less than a quarter as much as was lost from the EO water in Soo-Voo Len after about 2 months (40%).

Comparison of ANW with Electrolyzed Oxidizing (EO) Water of Shun-Yao Hsu

The stability of ANW in closed conditions at around 30° C. was compared with the stability of EO water as reported in the article "*Effects of storage conditions on chemical and physical properties of electrolyzed oxidizing water*"—Journal of Food Engineering 65 (2004) 465-471 by Shun-Yao Hsu, et al.

In Shun-Yao Hsu, the electrolyzed water of "formulation J" had an acidic pH (2.61), OPR=1147 mV, and a free chlorine content of 56 ppm. The article reports that in a closed condition at 25-30° C., the free chlorine in the electrolyzed water was 43 ppm after 21 days, a 23% loss. In comparison, ANW samples stored in closed conditions at 25° C., 30° C., and 40° C. without agitation lost 8.44%, 8.64%, and 15.43% of free chlorine after 3 months and 12.14%, 19.13%, and 18.31% of free chlorine after 1 year, respectively.

Example 6

The properties and composition of Acidic Nanoclustered Water were tested and found to have specifications as reported below in Table 11. The properties and composition Acidic Nanoclustered Water were also analyzed as reported below in Table 12.

TABLE 11

| Acid Water Specifications | | |
|---|---|---|
| Test Item | Method | Specification |
| Appearance | Naked eye | Liquid |
| Odour | Smell | Characteristic |
| Colour | Naked eye | Colourless |
| pH | as is @ 25° C. by Mettler Toledo pHmeter SevenMulti - Potentiometric Determination (Ph Eur. 2.2.3 - Current Ed.) | <3.00 |
| OxidoReductive Potential ORP (mV) | as is @ 25° C. by Mettler Toledo combination redox electrode (P/N 51343200) Potentiometric Tritation (Ph Eur. 2.2.20 - Current Ed.) | >1100.0 |
| Conductivity (uS cm$^{-1}$) | as is @ 25° C. | <1300 |
| Free Chlorine Assay (mg/l or ppm) | Internal Method M37-07 Spectrophotometric Method source APAT IRSA CNR HandBook Volume 2 - Ref 4080 | 40.0-70.0 |
| Total Chlorine Assay (mg/l or ppm) | Internal Method M37-07 Spectrophotometric Method source APAT IRSA CNR HandBook Volume 2 - Ref 4080 | 40.0-70.0 |

TABLE 11-continued

Acid Water Specifications

| Test Item | Method | Specification |
|---|---|---|
| Total Chlorine Assay (mg/l or ppm) | Internal Method M37-07 Iodometric Method source APAT IRSA CNR HandBook Volume 2 - Ref 4080 | 40.0-70.0 |
| Chloride Assay ((mg/l or ppm) | Internal Method M05-08 Spectrophotometric Method source APAT IRSA CNR HandBook Volume 2 - Ref 4090 | <200.0 |
| Chlorites (µg/l or ppb)) | EPA 300.1, 1997 (as $ClO_2$) | <100 |
| Chlorates (mg/l or ppm) | EPA 300.1, 1997 | <1 |
| $^{17}$O-NMR (Hz) Linewidth @ 50% | $^{17}$O-NMR Spectrometer | <50 |
| Heavy metals [Ag, As, Bi, Cd, Cu, Hg, Mo, Pb, Sb, Sn] | ICP Method | <10 ppm |
| Yttrium (ICP Method) | by EPA 200.8 1994 (0.1 µg/l detection limit) | <0.1 ppm |
| Zinc (ICP Method) | by EPA 200.8 1994 (0.1 µg/l detection limit) | <0.1 ppm |
| Iridium (ICP Method) | by EPA 200.8 1994 (0.1 µg/l detection limit) | <0.1 ppm |
| Titanium (ICP Method) | by EPA 200.8 1994 (0.1 µg/l detection limit) | <0.1 ppm |
| Zirconium (ICP Method) | by EPA 200.8 1994 (0.1 µg/l detection limit) | <0.1 ppm |
| Ruthenium (ICP Method) | by EPA 200.8 1994 (0.1 µg/l detection limit) | <0.1 ppm |

TABLE 12

Acid Water Test Results

| | ANW LOT LCOVI/57 | ANW LOT LCOX/5 | ANW LOT LCOX/1 |
|---|---|---|---|
| Appearance | colourless liquid with light chlorine smell (like swimming pool) | Same | Same |
| Free Chlorine Assay (mg/l) Spectrophotometric Method | 53.1 | 48.6 | 49.9 |
| Total Chlorine Assay (mg/l) Spectrophotometric Method | 52.1 | 48.6 | 49.0 |
| Total Chlorine Assay (mg/l) Iodometric Method | 60.6 | 54.9 | 56.7 |
| Chloride Assay (mg/l) UNI 24012 (Mercurimetric method) | 138 | 194.0 | 183.4 |
| Chlorites µg/l (as $ClO_2$) by EPA 300.1 1997 (detection limit 100 µg/l) | <100 | 100 | <100 |
| Chlorates mg/l by EPA 300.1 1997 (detection limit 0.1 mg/l) | 1.20 | 1.5 | 0.9 |
| pH (as is by Mettler Toledo pH meter Met Rohm 744) | 2.59 | 2.71 | 2.81 |
| ORP by Mettler Toledo PT4805-60-88TE-S7/120 combination redo electrode | 1151.8 | 1121.7 | 1110.5 |
| $^{17}$O NMR (Linewidth @ 50% - Hz) | 45.76 | 45.33 | 46.07 |
| Heavy Metals (Ag, As, Bi, Cd, Cu, Hg, Mo, Pb, Sb, Sn) | <10 ppm | <10 ppm | <10 ppm |

Example 6

The stability of Acidic Nanoclustered Water compositions containing different amounts of chloride ion were tested both in storage and in the open air. The low chloride composition contained less than 200 ppm chloride, and the high chloride composition contained 1100 ppm chloride.

To test storage stability, the compositions were stored in a closed condition at 25° C. and 60% relative humidity, and were not agitated or exposed to diffused light. After 3 and 12 months, the low chloride composition had a loss of free chlorine of 8.44% and 12.14%, respectively. In contrast, the high chloride composition had a loss of free chlorine of 27.4% after only 3 months.

Figure 5:
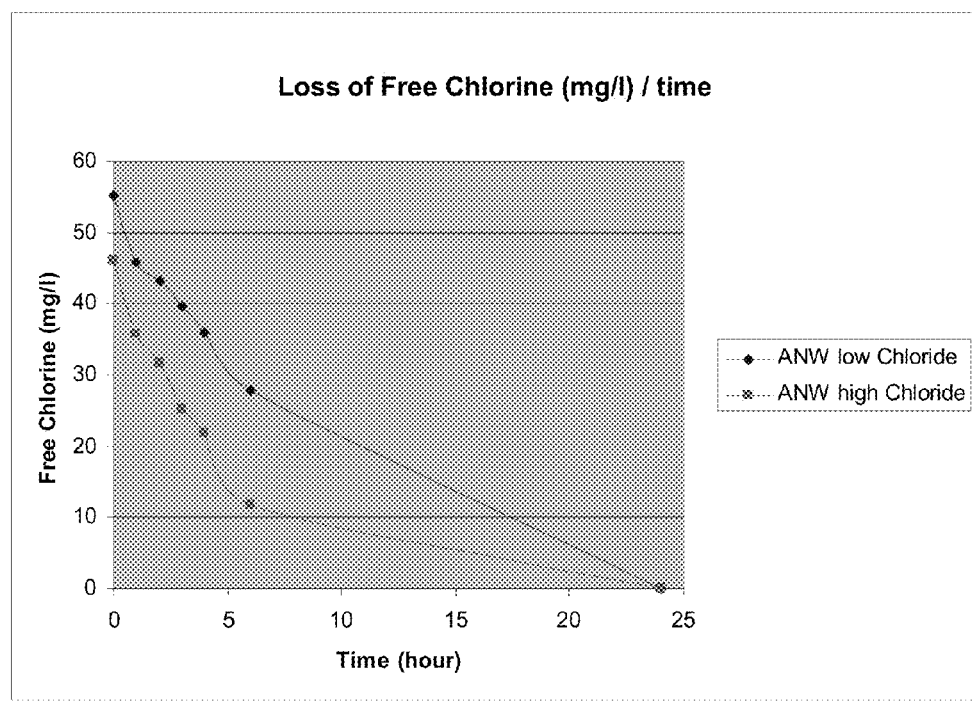
FIG. 5 is a graph illustrating the loss of free chlorine in high and low chloride Acidic Nanoclustered Water in an open, agitated, exposed condition over 24 hours.

To test open air stability, the two compositions were kept open, agitated, and exposed to light for 24 hrs at a temperature of 30° C. As illustrated in FIG. 5, the high chloride composition lost free chlorine at a greater rate than the low chloride composition.

These results demonstrate that the stability of ANW is dependent of chlorine remaining HClO, which prevents both evaporation and decomposition.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All references cited herein, including patents, patent applications, and published patent applications, are hereby incor-

The invention claimed is:

1. A method of treating cataract in a lens in an animal patient in need thereof, comprising topically administering to an eye of said patient a composition comprising a therapeutically effective amount of a high ORP acidic water wherein:
   a) the high ORP acid water comprises free chlorine, and
   b) from 95% to 99.9% of said free chlorine is present in the form of hypochlorous acid;
   c) said water has a pH of from 1.0 to 4.0; and
   d) said water has an ORP of greater than 1100 mV.

2. The method of claim 1, wherein said high ORP acidic water has an ORP of greater than 1100 mV, and a pH of from 0.5 to 5.0.

3. The method of claim 1, wherein said high ORP acidic water has a NMR half line width using $^{17}O$ of from 42 to 60 Hz, and a pH of about 0.5 to about 5.0.

4. The method of claim 1, wherein said administering step comprises dropping said composition directly into said eye.

5. The method of claim 1, wherein said administering step comprises applying said composition to said eye with a piece of gauze.

6. The method of claim 1, wherein said administering step comprises applying said composition to said eye 1 to 20 times per day, for at least 14 days.

7. The method of claim 1 wherein:
   a) from 90% to 99.9% of said free chlorine is present in the form of hypochlorous acid;
   b) said water has a pH of from 1.0 to 4.0; and
   c) said water has an ORP of greater than 1100 mV.

8. The method of claim 1 wherein the relative amount of HOCl and $Cl_2$ is from 99.9% HOCl and 0.1% $Cl_2$ to 95% HOCl to 5% $Cl_2$.

9. The method of claim 1 wherein the relative amount of HOCl and $Cl_2$ is from 99.5% HOCl and 0.5% $Cl_2$ to 98.5% HOCl to 1.5% $Cl_2$.

10. The method of claim 1 having a NMR half line width using $^{17}O$ of from 42 to 60 Hz.

11. The method of claim 1 wherein said water has a conductivity of from 1200 to 1400 uS/cm.

12. The method of claim 1 wherein said water maintains 90% of said free chlorine after a storage period of 3 months at room temperature.

13. The method of claim 1 wherein said water maintains 80% of said free chlorine after a storage period of 3 months at room temperature.

* * * * *